United States Patent [19]
Roberts

[11] Patent Number: 6,039,928
[45] Date of Patent: Mar. 21, 2000

[54] WRITING IMPLEMENT STERILIZATION APPARATUS

[76] Inventor: Jon L. Roberts, 529 Clear Spring Rd., Great Falls, Va. 22066

[21] Appl. No.: 09/014,559

[22] Filed: Jan. 28, 1998

[51] Int. Cl.[7] .................................................. B01J 19/00
[52] U.S. Cl. .......................................................... 422/186.3
[58] Field of Search ............................................. 422/186.3

[56] References Cited

U.S. PATENT DOCUMENTS

| | | | |
|---|---|---|---|
| 3,954,407 | 5/1976 | Andary et al. | 21/83 |
| 4,088,445 | 5/1978 | Ellis | 21/83 |
| 4,100,415 | 7/1978 | Blaisdell et al. | 250/455 |
| 4,625,119 | 11/1986 | Murdock, III | 250/455.1 |
| 4,694,180 | 9/1987 | Salisbury et al. | 250/455.1 |
| 4,772,795 | 9/1988 | Sakurai et al. | 250/455.1 |
| 4,803,364 | 2/1989 | Ritter | 250/455.1 |
| 4,806,770 | 2/1989 | Hylton et al. | 250/455.1 |
| 4,888,487 | 12/1989 | Ritter | 250/455.1 |
| 4,906,851 | 3/1990 | Beasley | 250/455.1 |
| 4,973,847 | 11/1990 | Lackey et al. | 250/455.1 |
| 5,023,460 | 6/1991 | Foster, Jr. et al. | 250/455.1 |
| 5,126,572 | 6/1992 | Chu | 250/455.11 |
| 5,127,521 | 7/1992 | Bourque | 206/362.1 |
| 5,487,877 | 1/1996 | Choi | 422/300 |
| 5,547,635 | 8/1996 | Duthie, Jr. | 422/24 |

*Primary Examiner*—Kathryn Gorgos
*Assistant Examiner*—Josephine Marsano
*Attorney, Agent, or Firm*—Roberts Abokhair & Mardula LLC

[57] ABSTRACT

A writing implement sterilization apparatus having ultraviolet sterilization in an enclosed container to kill bacteria and other disease carrying organisms. The invention comprises a horizontal or vertical container into which a user places pens, pencils, or other writing implements to be sterilized. An ultraviolet source within the container irradiates the writing implement thereby killing any microorganisms that might reside on the writing implements. Ultraviolet radiation below 200 nm can also be used thereby creating ozone gas having germicidal characteristics. The ozone gas is circulating in and around the writing implements thereby providing further sterilization together with the ultraviolet radiation. An interlocking switch turns the UV source off when the container is opened.

26 Claims, 4 Drawing Sheets

WRITING IMPLEMENT STERILIZATION APPARATUS

FIELD OF THE INVENTION

The present invention relates generally to sterilization devices. More particularly this invention relates to a device for sterilizing writing implements of all types using ultraviolet radiation in a closed container.

BACKGROUND OF THE INVENTION

It has long been known that germs are spread by, among other things, hand to hand contact. Hence there's been much in the literature recently concerning the washing of hands in order to prevent the spreading of the common cold as well as other microbes. Further, it has long been known that toothbrushes can be a source of the spreading of germs as well. Recently, it has been discovered that bacteria continue to live on writing implements there used by individuals. As such, writing implements can also carry microbes and therefore can be a vector for the spread of disease.

There is much prior art for the sterilization of various objects. For example, hospitals use sterilization routinely for surgical instruments. Typically such sterilization occurs both chemically as well as through high-pressure high temperature steam sterilization. This results in generally sterile instruments for use in surgery. The difficulty, of course, is that such devices are expensive, cumbersome, and are therefore not practical for the widespread sterilization of more common devices.

The spread of germs via bathroom articles has been the subject of invention. Many inventors have dealt with the issues associated with toothbrush sterilization. For example, U.S. Pat. No. 3,954,407 to Andary et al. discloses an automatic toothbrush sterilization comprising ultraviolet lamps. Similarly U.S. Pat. No. 4,088,445 to Ellis discloses a sterilization holder and night light for toothbrushes. U.S. Pat. No. 4,884,072 Ritter discloses a toothbrush sterilizer with automatic control. U.S. Pat. No. 4,772,795 to Sakurai et al. discloses an ultraviolet sterilizer for dental implements. U.S. Pat. No. 4,803,364 to Ritter discloses a toothbrush conditioner comprising an ultraviolet radiation source. U.S. Pat. No. 4,806,770 to Hylton et al. discloses another form of toothbrush holder having an ultraviolet lamp mounted within the housing.

U.S. Pat. No. 4,906,851 to Beasley et al. discloses yet another form of ultraviolet toothbrush sterilizer and holder. U.S. Pat. No. 4,973,847 to Lackey et al. discloses a toothbrush sanitation device having ultraviolet light source and a removable lid. U.S. Pat. No. 5,023,460 to Foster, Jr. et al. discloses a toothbrush sanitizer having a centrally mounted ultraviolet bulb with cavities for receiving toothbrushes. U.S. Pat. No. 5,126,572 to Chu discloses a toothbrush holder also having an ultraviolet source. U.S. Pat. No. 5,127,521 to Bourgue discloses a toothbrush holder also having an ultraviolet light source. U.S. Pat. No. 5,487,877 to Choi discloses a rest room organizer having a sterilization apparatus using ultraviolet light for sterilizing bathroom articles. U.S. Pat. No. 5,547,635 to Duthei, Jr. discloses a general sterilization method and apparatus wherein microorganisms are exposed to ultraviolet light. Thus it can be seen that much work has been done with respect to the sterilization of bathroom articles. However no attention has been paid to the sterilization of more common implements, specifically writing implements which have also been shown to carry disease producing microbes.

It would therefore be desirable to have a convenient, commonly available, inexpensive, and easy to use sterilization method and apparatus for sterilizing writing implements thereby preventing the transmission of object-borne disease spreading microorganisms.

SUMMARY OF THE INVENTION

It is therefore an object to the present invention to sterilize commonly used writing implements such as pencils and pens.

It is a further object of present invention to provide a writing implement sterilization apparatus that can be commonly available and easy to use.

It is a further object of the present invention to provide a sterilization apparatus using ultraviolet radiation as a means of sterilization.

It is a further object of present invention to combine ultraviolet sterilization and ozone sterilization together to completely sterilize writing implements.

It is a further object impressed invention to provide a sterilization device for sterilizing writing implements safely and without exposing a user to ultraviolet sterilization radiation.

It is a further object of a present invention to provide a writing implements sterilization unit that operates on normal wall current or battery power.

These and other objects of the present invention will become apparent to those skilled in the art by review of the specification that follows.

The present invention is a convenience, compact, and easy to use writing implement sterilization unit. The present invention comprises generally an ultraviolet light source particularly in the 200 to 300 nm wavelength range. This range has long been known for its germicidal and sterilization effects achieved by direct radiation. It is also well-known that ultraviolet radiation below 200 nm can produce small quantities of ozone from oxygen in the atmosphere. Ozone, in sufficient concentrations is known to have significant germicidal and sterilization effects. Further, ozone, as a gas, is able to reach certain places and crevices in writing implements where ultraviolet radiation might not reach, especially when a number of writing implements are being sterilized together simultaneously.

The ultraviolet light source of the present invention is mounted within a housing such that the ultraviolet radiation can shine directly upon and reflect onto writing implements that are also disposed within the housing. Thus the interior of the housing also can reflect ultraviolet radiation in directions such as to both directly and indirectly reach all parts of the writing implements to be stylized.

The ultraviolet light source can be mounted in a number of configurations. For example where the writing implement sterilization apparatus is disposed vertically, the ultraviolet lamp can be a ring type lamp at the top of the housing, a tubular ultraviolet lamp source that can stand vertically in the housing, a series of ultraviolet lamps that can be disposed around the perimeter of the housing thereby directing radiation inward to writing implements that are contained vertically or horizontally within the housing.

Alternatively the writing implements sterilization apparatus can be disposed horizontally with writing implements simply laid down horizontally inside the horizontal housing. In this instance, an ultraviolet light source could be disposed underneath the writing implement support with the ultraviolet radiation shining upward. Ultraviolet light sources also could be mounted in an upper lid which is closed over the writing implements allowing ultraviolet light to shine downward over the writing implements. Alternatively the ultraviolet radiation could come from both above and below the writing implements thereby completely immersing them in sterilizing, germicidal ultraviolet rays.

The wavelength range of the ultraviolet radiation of the present invention also causes a small amount of ozone to be generated. This ozone is released into the housing and together with the ultraviolet radiation provides a more complete sterilization of the writing implements.

The present invention also comprises the top or lid which is hingedly or removably attached in to the lower sterilization housing. This cover or lid prevents ultraviolet radiation from escaping the container thereby protecting any users or those who pass by the sterilization apparatus.

Integral to the housing and its cover, is an interlocking switch which is biased in the "off" position. When the cover is placed over the sterilization apparatus, the switch is engaged and the ultraviolet radiation light source is turned on. When the cover is removed, for example when a writing implement is withdrawn from housing, the ultraviolet radiation is immediately turned off as soon as the cover is removed or the lid is lifted.

A timer circuit for the ultraviolet light source is also part of present invention. The timing circuit is activated as soon as the cover or lid of the sterilization apparatus is closed and the interlocking switch is engaged. The timer allows the ultraviolet light source to remain on for a predetermined amount of time. This time is consistent with complete sterilization of writing implements contained within the apparatus of the present invention. When the amount of time has expired, the ultraviolet light source is turned off thereby saving both power as well as prolonging the life of the ultraviolet light source(s). In the event that the cover or lid is lifted, as in the removal of writing implements, the timer is reset and, upon closing of the lid, the sterilization time period begins again.

The present invention allows for writing implements to be supported either by a screen or other porous and/or transparent material that can both support the writing implements as well as allow the passage of ultraviolet light and ozone. Alternatively the present invention comprises a quartz tray such that the ultraviolet light is allowed to pass through the quartz supporting tray while still supporting the writing implements. In those cases where a quartz supporting mechanism is used, sufficient gaps between the housing and quartz supporting mechanism is present to allow ozone gas to diffuse among the writing implements thereby providing further sterilization. Alternatively, apertures or holes in the quartz tray are provided to allow the passage of ozone gas.

As integral part of the sterilization, an indicator light is provided whereby, when sterilization is proceeding, the indicator light is lit. When sterilization is not occurring, as in the case when the lid is lifted or the sterilization lamp has burned out, the indicator light is not lit. In this case it will be clear to the user that either maintenance on the device must occur or the lid is not properly engaged with the interlocking switch.

The present invention can operate both on normal current found in homes, businesses, and buildings of all types as well as on battery power. Where battery power is used it is anticipated that rechargeable batteries will be present in the present invention such that sterilization can continue to take place for some period of time even during power failures.

BRIEF DESCRIPTION OF THE DRAWINGS

The present invention is now described by way of example with references to the accompanying drawings.

Figure 1:
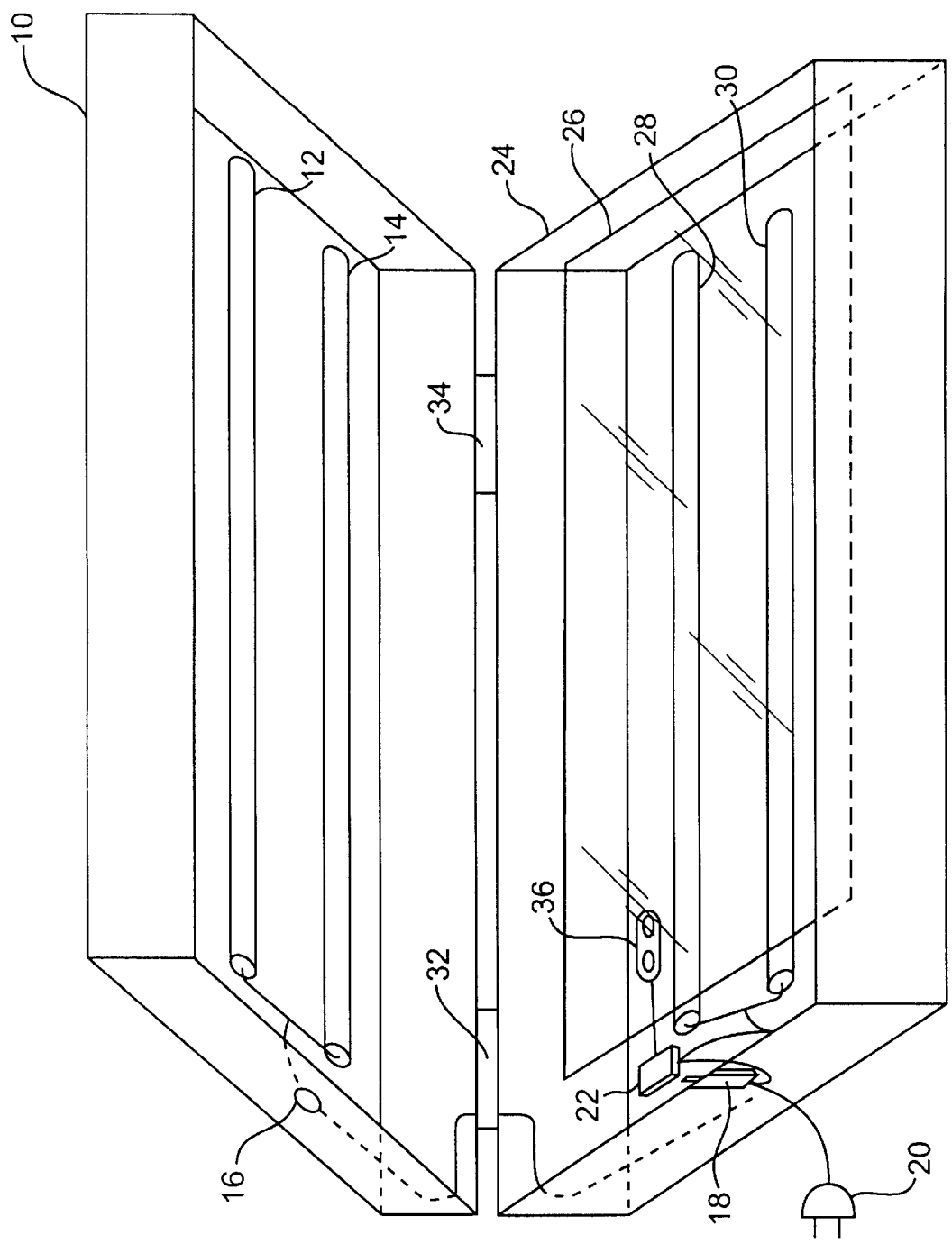
FIG. 1 Shows a horizontally disposed version of the present invention

The sterilization apparatus receives power from the typical wall outlet via a plug 20 which is attached to an interlocking switch 18. This switch is biased in the "off" position so that when upper lid 10 in the open position all lamps 28, 30, 12 and 14 are off. Conversely, when the upper lid is closed, switch 18 is closed and power is provided to lamps 28, 30, 12 and 14. Further when all lamps are lit indicator light 16 is also lit showing anyone viewing the apparatus that ultraviolet radiation is being generated by the lamps contained in the apparatus. It should be noted that the position of indicator lights 16 is entirely arbitrary and can be placed anywhere on the apparatus to provide satisfactory convenient viewing by the user.

Writing implements are supported by the supporting means 26 which is of a transparent and/or porous material. This supporting means may be a quartz plate or any other material that allows transmission of the ultraviolet radiation generated from lamps 28 and 30 which are disposed below the supporting means 26. Further, supporting means 26 may also have circulation apertures in the supporting means to allow circulation of air within the sterilization apparatus.

As noted earlier, ultraviolet radiation in the 200 nm range generates ozone gas. In sufficient quantities ozone gas can have a germicidal effect. Therefore apertures in the supporting means 26 are provided to allow circulation of the ozone gas so that additional germicidal effects in addition to those of the ultraviolet radiation may occur. To further enhance circulation of air within the apparatus a small circulation fan 36 is provided. This fan is actuated when the interlocking switch 18 is actuated thereby providing power to the apparatus.

As part of the preferred embodiment, a timer circuit 22 is also provided. This timer circuit activates the ultraviolet sterilization lamps 12,14, 28, and 30 as well as the recirculating fan 36 for a specific period of time. This period of time can be preset based upon the optimum time necessary to achieve sterilization. In the event that the upper lid 10 is not opened within the time period established in the timer circuit 22 the sterilization lamps will go off after the passage of the optimum sterilization time. In event that the upper lid 10 is opened before the time for sterilization has expired, the timer 22 is reset and, when the upper lid 10 is closed, the sterilization period begins again. In this fashion power to sterilization lamps 12, 14, 28, and 30 is turned off after the appropriate sterilization period thereby saving lamp life and prolonging useful life of the ultraviolet sterilization lamps.

Figure 2:
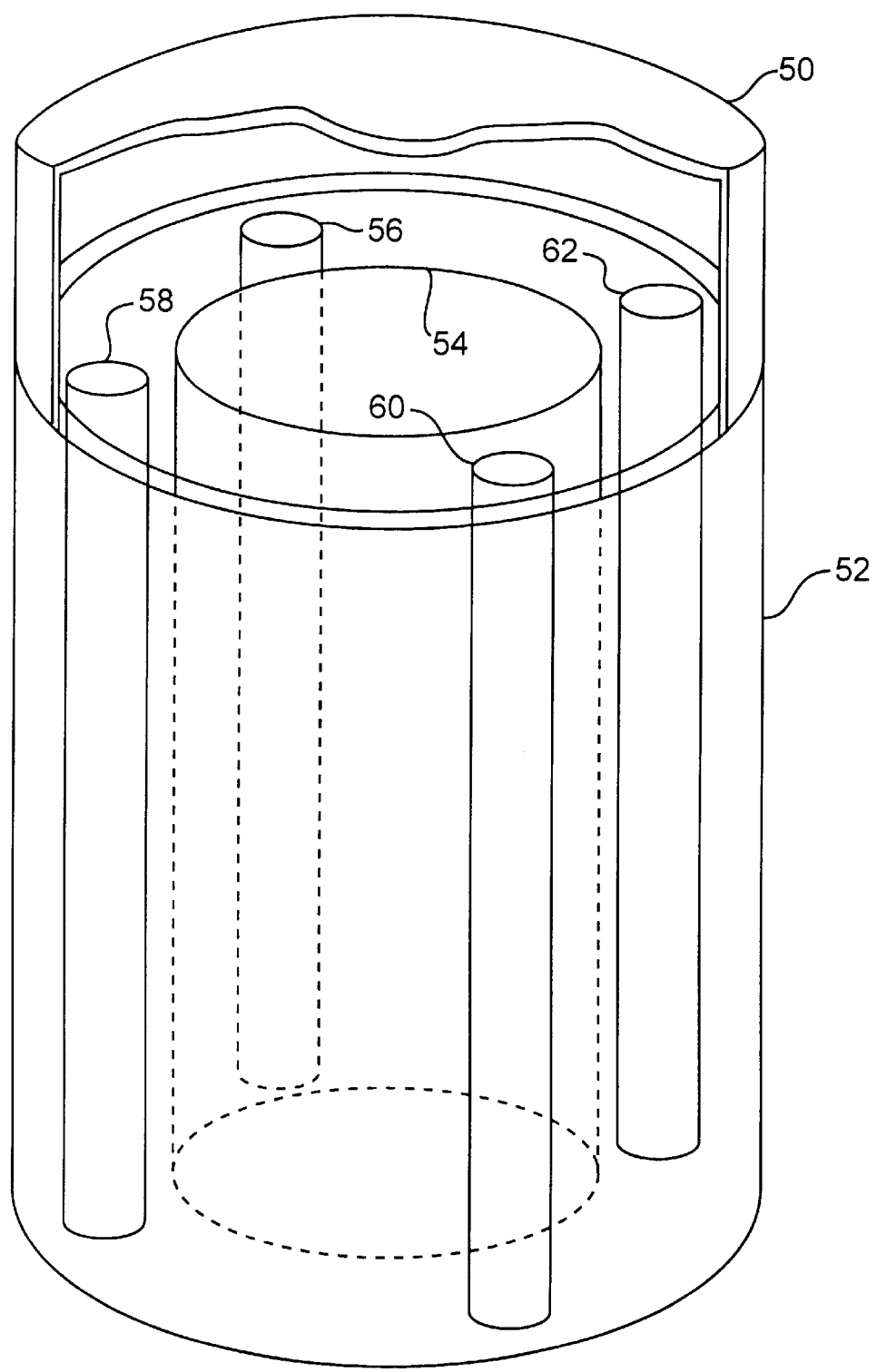
FIG. 2 Shows a vertically disposed version of the present invention

Referring to FIG. 2 an alternative vertical embodiment of the present invention is shown. In this case an inner cylinder 54 which comprises a quartz material or any other material that is transparent to ultraviolet radiation is disposed inside an outer cylinder 52. Ultraviolet sterilization lamps 56, 58, 60, and 62 are disposed between a inner cylinder and the outer cylinder. Light from the sterilization lamps is directed into the inner cylinder 54 in which writing implements may be placed. Upper lid 50 is removably attached to the lower cylinder 52.

It should be noted that the number of sterilization lamps depicted in FIG. 2 is arbitrary. More lamps could be used depending upon the configuration and size of the inner and outer cylinders. For example, a ring-shaped lamp could be disposed in the bottom of the cylinder and the upper lid thereby shining UV radiation both up and down the length of the writing implements to be sterilized. However, a sufficient number of lamps to achieve the sterilization desired must be used.

Again an interlocking switch (not shown) is actuated when upper lid 50 is placed over lower cylinder 52 thereby providing power to the sterilization lamps 56, 58, 60, and 62. In addition, a circulation fan (not shown) is provided with the vertical embodiment to circulate any ozone produced by the sterilization lamps within the container. Power is provided to the vertical embodiment of FIG. 2 from conventional household power. A battery backup is also anticipated in event of power failure. In order to assistant in the circulation of ozone, inner cylinder 54 has apertures through the walls of the cylinder to allow for circulation of ozone gases produced by the sterilization lamps in and around the writing implements to be sterilized.

Figure 3:
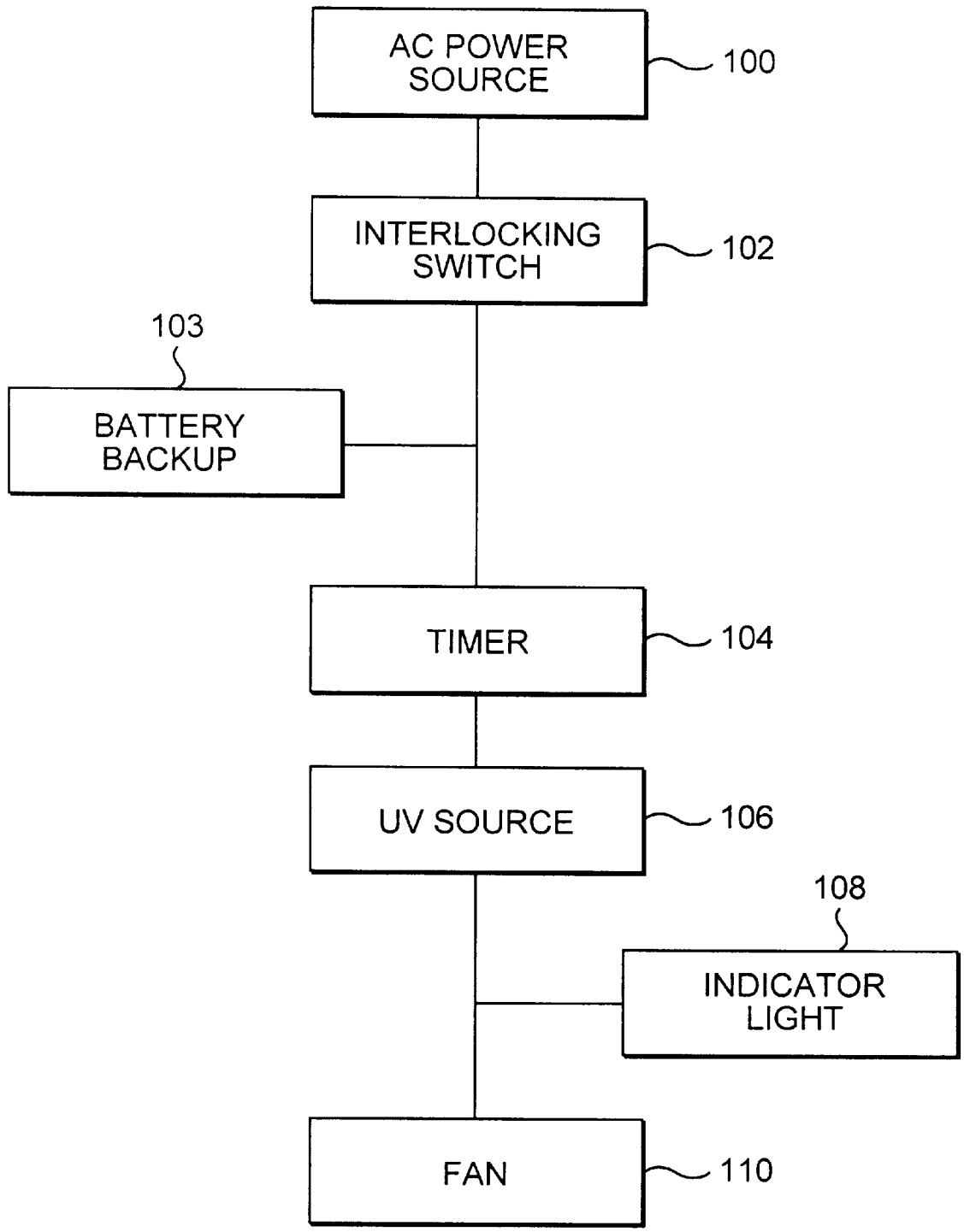
FIG. 3 is a simple schematic of the circuitry of the present invention

Referring to FIG. 3 a simplified circuit diagram of the present invention is shown. Power from conventional household power 100 is provided to the sterilization unit. Power is provided directly to the interlocking switch 102 so that when the upper lids of the various embodiments are closed, power is provided to the entire device. A battery 103 is also provided such that power from the wall outlet also recharges the battery 103. Power then flows to the timer circuit 104 which is preset to an optimum sterilization time. When switch 102 is actuated and timer 104 begins, power is applied to the sterilization lamp(s) 106. As noted earlier it is anticipated that numerous configurations of sterilization lamps in both size, physical shape, and number are anticipated as within the scope of the present invention.

Whenever the sterilization lamp(s) 106 is lit indicator lamp 108 is also lit thereby noting to users that ultraviolet radiation is being produced. If sterilization lamp(s) 106 is not lit either because the lamp has burned out or switch 102 is in the open position, indicator light 108 is not lit. When the power is again provided to the sterilization lamp(s) 106, indicator light 108 is also lit.

In addition, whenever power is applied to sterilization lamp(s) 106 a small circulation fan 110 is also actuated thereby circulating any ozone gas that is produced by the UV lamps of the present invention. This gas circulates in and around the writing implements that are being sterilized.

Figure 4:
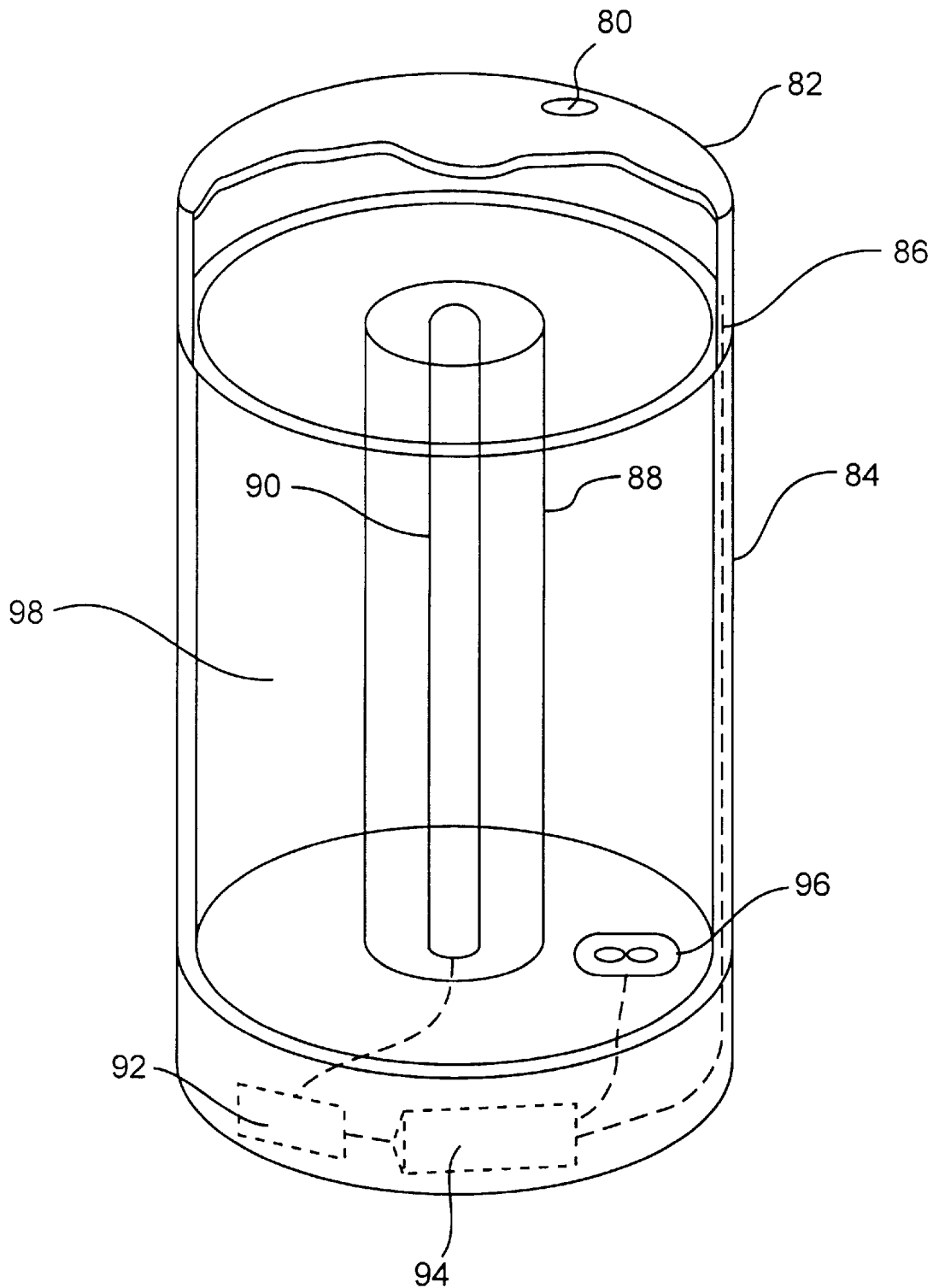
FIG. 4 Shows a vertically disposed version of the present invention with a central vertical UV source Referring to FIG. 1 a horizontal embodiment of the present invention is shown. The sterilization apparatus of the present invention comprises the top lid 10 hingedly attached to a lower container 24 by hinges 32 and 34. Ultraviolet lamps 12 and 14 are attached to the top lid 10. Another pair of ultraviolet lamps to 28 and 30 are located in and attached to the floor container 24. It should be noted that the number of lamps depicted in FIG. 1 is not meant to be limiting. For example in certain embodiments it may be more appropriate to have more than two lamps in the upper lid and the lower container portion. Further while the lamps are shown as individual tube type lamps, alternative shapes are well within the state-of-the-art including U-shaped lamps, ring-shaped lamps individual bulb-type lamps, and indeed any other lamp that will emit the appropriate ultraviolet radiation necessary for the sterilization.

Referring to FIG. 4 an alternative embodiment of the present invention is shown. Ultraviolet producing lamp 90 is positioned vertically inside a protective cylinder 88. The protective cylinder is both transparent to ultraviolet radiation and therefore may comprise quartz or any other material that has the appropriate transparency characteristics. Protective cylinder 88 also serves to protect the lamp 90 from any damage due to writing implements being placed within the sterilization apparatus.

The ultraviolet lamp 90 and protective cylinder 88 are placed within an outer container cylinder 84 which serves to be the container into which writing implements are placed for sterilization. Upper lid 82 is hingedly or removably attached to lower cylinder 84. Interlocking switch 86 is disposed in an "off" position such that when upper lid 82 is not placed over lower cylinder 84 power to the ultraviolet lamp 90 is not provided. This insures the safety of users so that they are not exposed to any ultraviolet radiation. Whenever upper lid 82 is placed over cylinder 84 thereby actuating interlocking switch 86 an indicator light 80 is lit thereby showing a user that power is being supplied to the sterilization lamps within the sterilization apparatus.

As in other alternative embodiments, timer circuit 94 allows both power and timed illumination to occur. Timer circuit 94 allows power to reach circulation fan 96 which circulates the air within the present invention thereby circulating any ozone gas produced by the UV lamps in and around any writing implements that are being sterilized. This provides an additional measure of germicidal sterilization of the writing implements stored within present invention. So long as the time is not expired in timer circuit 94 power is provided to the power circuit 92 which allows sterilization lamp 90 to be lit.

A method and apparatus for sterilization of writing implements has been shown. Various alternative embodiments of the present invention have also been shown by reference to the figures contained herein. Common to all of these embodiments are the sterilization lamps, means for supporting writing implements in such a fashion that ultraviolet radiation can reach the various writing implements to sterilize them, circulation means to circulate in any ozone produced by the ultraviolet lamps, and power and timing circuits to provide timed sterilization for writing implements that are stored in the sterilization apparatus of the present invention.

It will be appreciated by those skilled in the art that other embodiments may be possible employing the common elements of the present invention that has been disclosed.

What is claimed is:

1. A writing implement sterilization apparatus comprising:

a container;

a lid attached to the container;

a first source of ultraviolet radiation disposed within the container;

a writing implement holder for supporting writing implements disposed within the container;

a power supply connected to the first source; and an interlocking switch, connected between the power supply and the first source and being biased to the off position, such that when the lid is in an open position the interlocking switch is not engaged and no power is supplied to the first source and when the lid is closed, the interlocking switch is engaged and power is supplied to the first source.

2. The writing implement sterilization apparatus of claim 1 wherein the first source emits ultraviolet radiation below 200 nm and creates ozone gas.

3. The writing implement sterilization apparatus of claim 2 wherein the first source comprises a plurality of ultraviolet emitting lamps.

4. The writing implement sterilization apparatus of claim 2 wherein the writing implement holder is transparent to ultraviolet radiation.

5. The writing implement sterilization apparatus of claim 4 wherein the writing implement holder further comprises air circulation apertures for allowing the circulation of the ozone produced by ultraviolet radiation emitted by the first source.

6. The writing implement sterilization apparatus of claim 5 further comprising an air circulation fan for circulating ozone through the circulation apertures and throughout the container.

7. The writing implement sterilization apparatus of claim 1 wherein the first source emits ultraviolet radiation above 200 nm.

8. The writing implement sterilization apparatus of claim 7 wherein the first source comprises a plurality of ultraviolet emitting lamps.

9. The writing implement sterilization apparatus of claim 7 wherein the writing implement holder is transparent to ultraviolet radiation.

10. The writing implement sterilization apparatus of claim 1 wherein the container is oriented vertically to allow the writing implements to be placed vertically therein for sterilization.

11. The writing implement sterilization apparatus of claim 1 wherein the container is oriented horizontally to allow the writing implements to be placed horizontally therein for sterilization.

12. The writing implement sterilization apparatus of claim 1 wherein the first source comprises at least one ultraviolet emitting lamp.

13. The writing implement sterilization apparatus of claim I further comprising an indicator light connected to the interlocking switch and the first source such that the indicator light is lit only when the interlocking switch is engaged and the first source is illuminated.

14. The writing implement sterilization apparatus of claim 1 wherein the power supply comprises a battery.

15. The writing implement sterilization apparatus of claim 14 wherein the battery is rechargeable and is recharged by the power supply.

16. A writing implement sterilization apparatus comprising:
    a container;
    a lid attached to the container;
    a first source of ultraviolet radiation, disposed within the container;
    a second source of ultraviolet radiation, disposed within the lid;
    a writing implement holder for supporting writing implements disposed within the container;
    a power supply connected to the first source; and
    an interlocking switch, connected between the power supply and the first source and being biased to the off position, such that when the lid is in an open position the interlocking switch is not engaged and no power is supplied to the first source and when the lid is closed, the interlocking switch is engaged and power is supplied to the first source.

17. The writing implement sterilization apparatus of claim 16 wherein the interlocking switch further controls power to the second source.

18. The writing implement sterilization apparatus of claim 16 where the second source emits ultraviolet radiation below 200 nm.

19. The writing implement sterilization apparatus of claim 16 where the second source emits ultraviolet radiation above 200 nm.

20. A writing implement sterilization apparatus comprising:
    a substantially vertically oriented container for vertical placement of writing implements;
    a lid attached to the substantially vertically oriented lower container;
    a substantially vertically oriented ultraviolet radiation source disposed within the container for sterilizing writing implements contained therein;
    a substantially vertically oriented writing implement holder for supporting writing implements disposed within the container;
    a power supply connected to the ultraviolet radiation source; and
    an interlocking switch, connected between the power supply and the ultraviolet radiation source and being biased to the off position, such that when the lid is in an open position the interlocking switch is not engaged and no power is supplied to the ultraviolet radiation source and when the lid is closed, the interlocking switch is engaged and power is supplied to the ultraviolet radiation source.

21. The writing implement sterilization apparatus of claim 20 wherein the ultraviolet radiation source emits ultraviolet radiation below 200 nm and creates ozone gas.

22. The writing implement sterilization apparatus of claim 21 further comprising a circulation fan for circulating the ozone gas throughout the container.

23. The writing implement sterilization apparatus of claim 20 wherein the ultraviolet radiation source emits ultraviolet radiation above 200 nm.

24. A writing implement sterilization apparatus comprising:
    a substantially horizontally oriented container for horizontal placement of writing implements;
    a lid attached to the substantially horizontally oriented container;
    a substantially horizontally oriented ultraviolet radiation source disposed within the container for sterilizing writing implements contained therein;
    a substantially horizontally oriented writing implement holder for supporting writing implements disposed within the container;
    a power supply connected to the ultraviolet radiation source; and
    an interlocking switch, connected between the power supply and the ultraviolet radiation source and being biased to the off position, such that when the lid is in an open position the interlocking switch is not engaged and no power is supplied to the ultraviolet radiation source and when the lid is closed, the interlocking switch is engaged and power is supplied to the ultraviolet radiation source.

25. The writing implement sterilization apparatus of claim 24 wherein the ultraviolet radiation source emits ultraviolet radiation above 200 nm.

26. The writing implement sterilization apparatus of claim 24 wherein the ultraviolet radiation source emits ultraviolet radiation below 200 nm and creates ozone gas.

* * * * *